(12) United States Patent
Spivey et al.

(10) Patent No.: US 8,857,990 B2
(45) Date of Patent: Oct. 14, 2014

(54) DEVICE AND PROCESS FOR PROGRESSIVE ADDITION LENS DESIGN

(76) Inventors: Brett Spivey, Carlsbad, CA (US); Andreas Dreher, Escondido, CA (US)

( * ) Notice: Subject to any disclaimer, the term of this patent is extended or adjusted under 35 U.S.C. 154(b) by 0 days.

(21) Appl. No.: 13/065,777

(22) Filed: Mar. 30, 2011

(65) Prior Publication Data

US 2012/0113393 A1    May 10, 2012

Related U.S. Application Data

(60) Provisional application No. 61/341,474, filed on Mar. 31, 2010.

(51) Int. Cl.
*A61B 3/02* (2006.01)
*A61B 3/04* (2006.01)
*G02C 7/06* (2006.01)

(52) U.S. Cl.
CPC .. *A61B 3/04* (2013.01); *G02C 7/061* (2013.01)
USPC .......................................... 351/228; 351/221

(58) Field of Classification Search
USPC ................................................. 351/221–228
See application file for complete search history.

(56) References Cited

U.S. PATENT DOCUMENTS

| | | | | |
|---|---|---|---|---|
| 4,784,482 A | * | 11/1988 | Guilino | 351/159.47 |
| 6,000,798 A | * | 12/1999 | Chipman et al. | 351/159.52 |
| 6,462,875 B1 | * | 10/2002 | Ishii | 359/576 |
| 6,538,978 B1 | * | 3/2003 | Holtslag et al. | 369/275.1 |
| 6,599,317 B1 | * | 7/2003 | Weinschenk et al. | 623/6.34 |
| 2002/0140899 A1 | * | 10/2002 | Blum et al. | 351/159 |
| 2003/0003295 A1 | * | 1/2003 | Dreher et al. | 428/332 |
| 2004/0041287 A1 | * | 3/2004 | Engardio et al. | 264/1.7 |
| 2004/0051846 A1 | * | 3/2004 | Blum et al. | 351/168 |
| 2004/0056986 A1 | * | 3/2004 | Blum et al. | 349/13 |
| 2004/0160574 A1 | * | 8/2004 | Dreher | 351/159 |
| 2007/0268452 A1 | * | 11/2007 | Dreher | 351/176 |
| 2008/0143960 A1 | * | 6/2008 | MacRae | 351/230 |
| 2008/0278681 A1 | * | 11/2008 | Blum et al. | 351/169 |
| 2009/0323182 A1 | * | 12/2009 | Gebelein | 359/407 |
| 2010/0277686 A1 | * | 11/2010 | Kurtin | 351/154 |

* cited by examiner

*Primary Examiner* — William Choi
*Assistant Examiner* — Sharrief Broome
(74) *Attorney, Agent, or Firm* — John R. Ross; John R. Ross, III

(57) ABSTRACT

A progressive addition lens design device for designing progressive addition lenses to permit a patient to experience a variety of distance vision fields and reading vision fields. The device includes a frame adapted to hold in place in front of each of a patient's eyes three lens mounts, each lens mounts being adapted for adjustment in rotation and side-to-side translation. A third lens displaying the patient's base prescription mounted in one of the lens. A first and second lens is mounted in the other two lens mounts. The first and second lenses, each have a transition zone and a power ramp zone and they have complementary surfaces so that when stacked together they create a standard progressive addition lens with a distance vision field, a reading vision field and transition region. When the first and second lenses are moved relative to each other the locations of the distance vision field, the reading vision field and the transition region are adjusted allowing the patient to experience a variety of distance vision fields, reading vision fields, and transition regions.

3 Claims, 5 Drawing Sheets

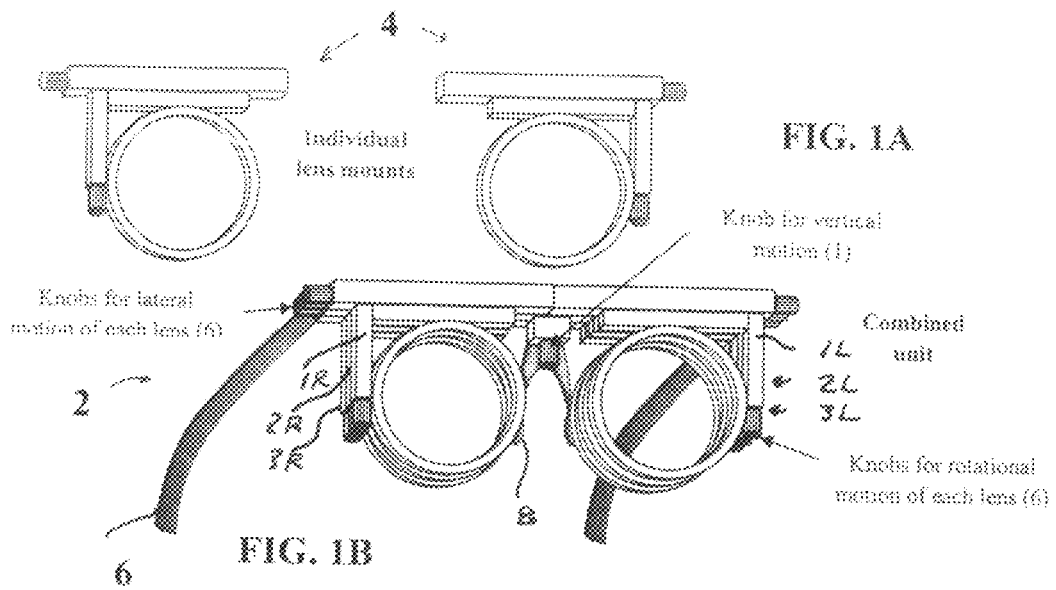
FIG. 1A
FIG. 1B
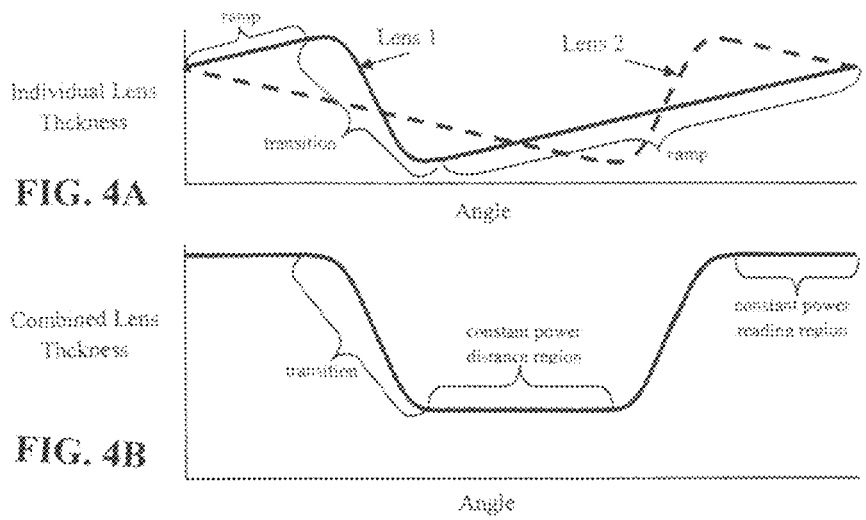
FIG. 4A
FIG. 4B

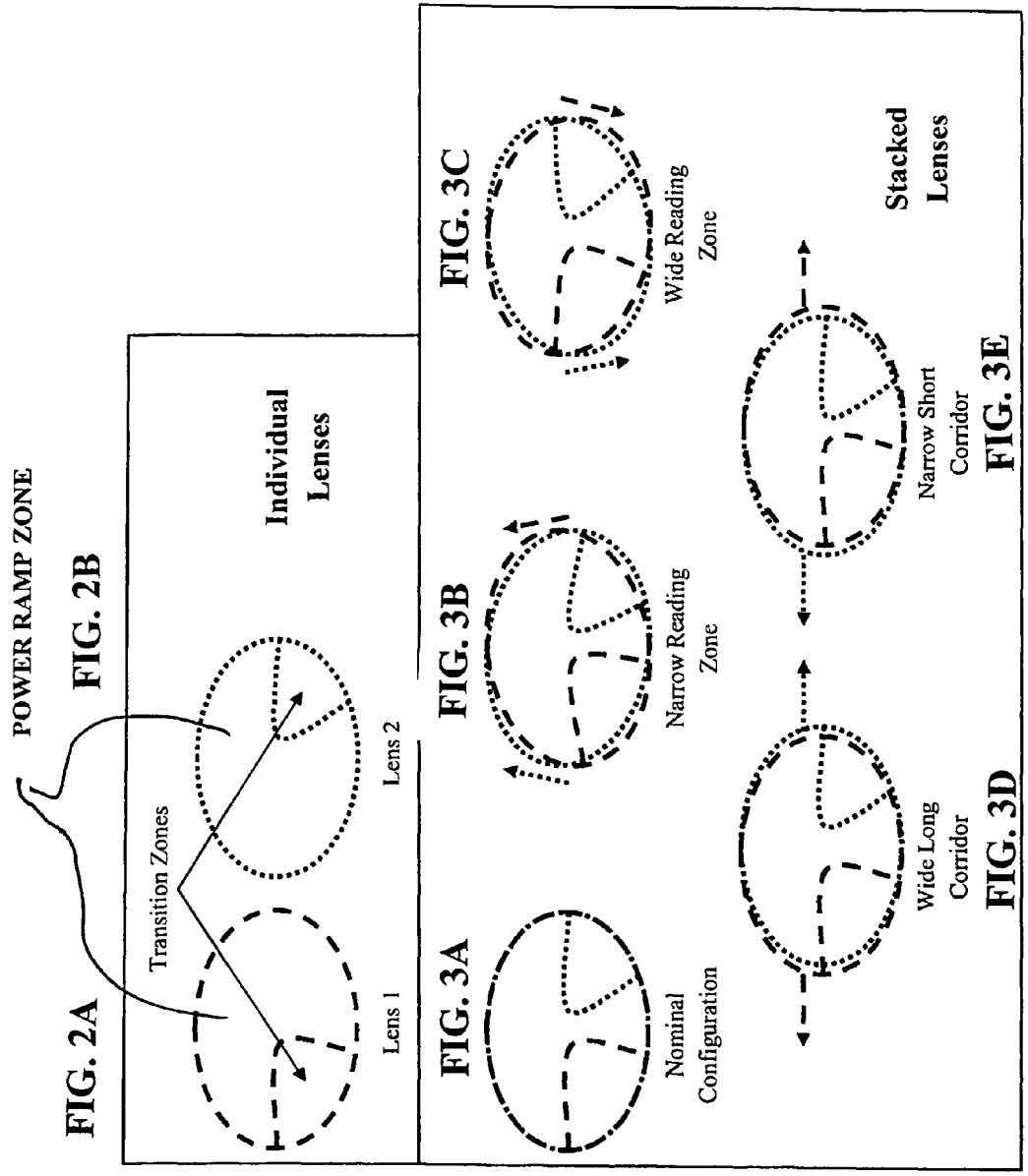

FIG. 6A  FIG. 6B
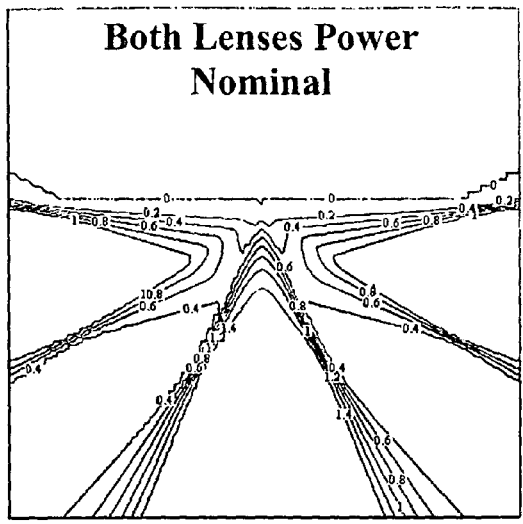
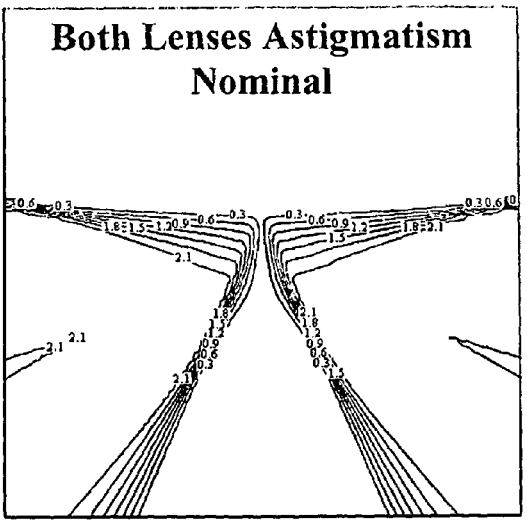
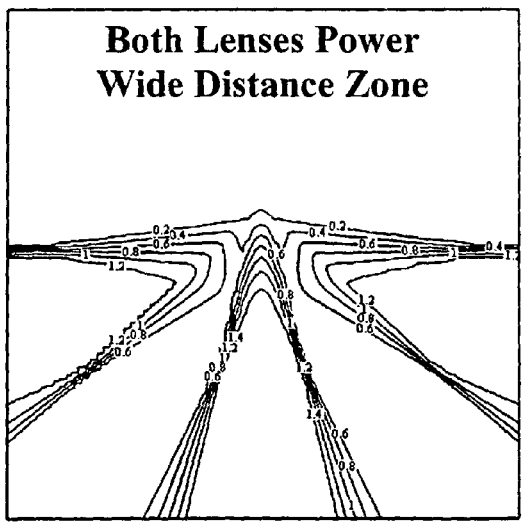
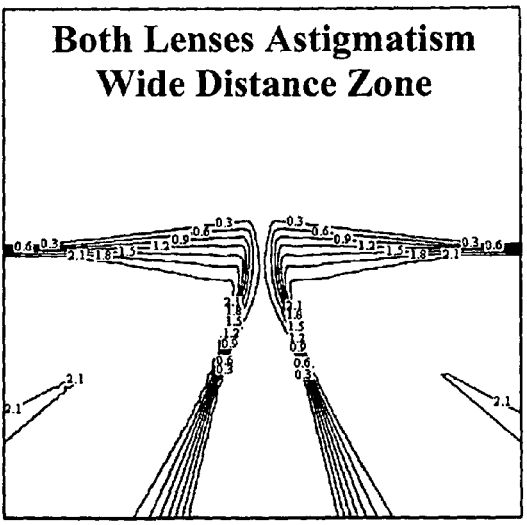
FIG. 6C  FIG. 6D

FIG. 6E
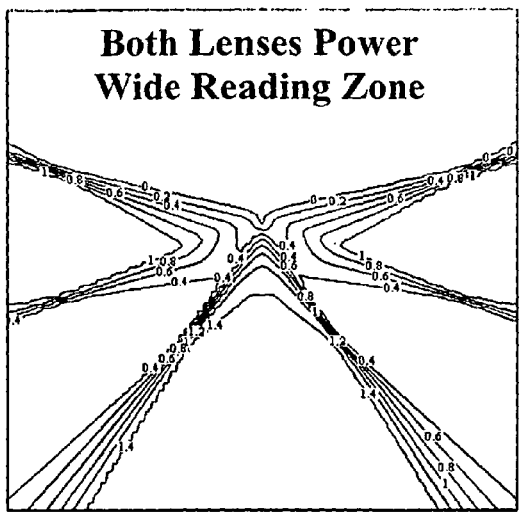
Both Lenses Power
Wide Reading Zone
FIG. 6F
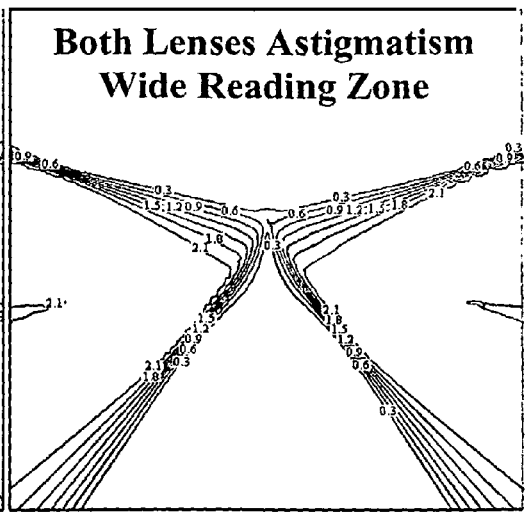
Both Lenses Astigmatism
Wide Reading Zone
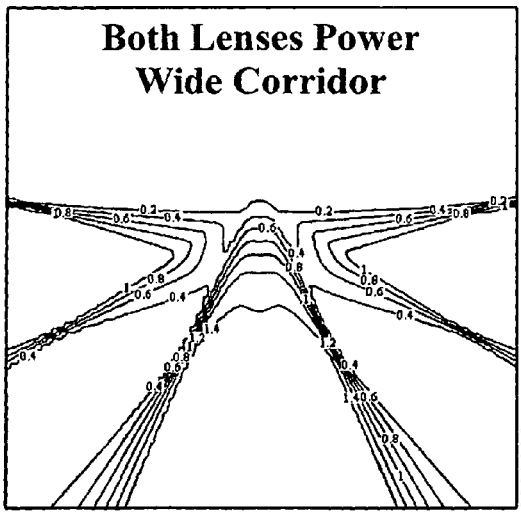
Both Lenses Power
Wide Corridor
FIG. 6G
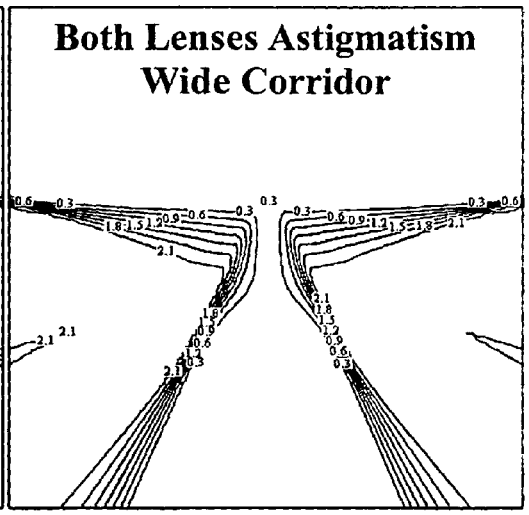
Both Lenses Astigmatism
Wide Corridor
FIG. 6H

DEVICE AND PROCESS FOR PROGRESSIVE ADDITION LENS DESIGN

CROSS REFERENCE TO RELATED APPLICATIONS

This application claims the benefit of Provisional Patent Application, Ser. No. 61/341,474, filed Mar. 31, 2010.

FIELD OF THE INVENTION

The present invention relates to progressive addition lenses and the processes for designing progressive addition lenses.

BACKGROUND OF THE INVENTION

When a patient is examined for prescription eyeglasses, there are some parameters measured by the optometrist or ophthalmologist which are accurately determined through an examination. This examination is usually carried out using a phoropter, autorefractor, or aberrometer to measure the patient's eye aberrations (expressed in power, cylinder, and angle) as well as other means to determine eye related parameters and patient eyeglass preference parameters like frame size, frame style, pupil distances, pupil heights, vertex distance, pantoscopic tilt, wrap angle, tint preference, color preference, material preference, UV blocking preference, antireflection coating preference, and high order aberration correction preference. If the patient is being prescribed a progressive addition lens (PAL), which includes bifocal, multifocal and progressive addition lenses, then also measured is the patient's accommodation, which is the ability of the eyes to change focus between distant and near objects. If a patient has presbyopia, he is impaired in his ability to focus on close objects.

A PAL design corrects a patient's eyesight, but also helps with the accommodation from near to far by including two or more regions on the eyeglass lens which have different add power. The distance zone is typically on the top part of the lens, and corrects for some or all of the eye's aberrations when focusing at a distant object. There is also a reading zone on the lower part of the lens, usually toward the nose, and usually smaller than the distance zone, which has typically 1-3 diopters of added sphere power compared to the distance zone. There is a smooth transition between these zones in a PAL and an abrupt transition in a bifocal or multifocal lens. The transition zone has aberrations (blurring) and distortions (bending or waviness) except in a fairly narrow channel called a "corridor" connecting the zones. In this corridor the sphere power varies smoothly at intermediate values between the distance and reading power.

There are some subjective parameters associated with a PAL design, however, which do not come out of the eye examination, and instead are currently determined through the prescriber's and patient's judgment about what the patient might prefer for their lifestyle or uses for the glasses. In particular, there are two key parameters which are vital to a patient's happiness with a particular progressive addition lens design:

1. The tradeoff between the size of the distance vision field and the near vision field. If the distance field is small, then there are distortions at the edge of the lenses which cause the so-called "swim effect" and can be unsettling. If the reading field is small, then there is a very limited close field of view which can make reading difficult. If neither is small, then the distortions and aberrations in the transition regions become excessive and unpleasant.

2. Tradeoff between the length and width of the corridor. If the corridor is short, then the width of the corridor is small, and the lenses are ineffective at intermediate zones. If the corridor is long, then it is wider, but the reading zone may then be too small or moved out of the frames.

Currently, manufacturers of PALs try to demonstrate these tradeoffs by showing the patient simulated images of what the patient might see when wearing glasses with PALs. However, these simulations cannot give the patient the experience of actually looking through the PALs and seeing the typical distortions. It is common practice to just manufacture a pair of glasses with Pals for a patient to try. Since a significant percentage of patients end up not liking those glasses, the current approach is expensive and wasteful.

What are needed are a device and a process for a patient to experience how a particular progressive addition lens will affect his vision, and for helping design progressive addition lenses to help establish the best tradeoff between the distance vision field and the near vision field to best satisfy particular patients.

SUMMARY OF THE INVENTION

The present invention provides a progressive addition lens demonstration device for demonstrating different progressive addition lenses to permit a patient to experience a variety of distance vision fields and reading vision fields. The device includes a frame adapted to hold in place in front of each of a patient's eyes three lens mounts, each lens mount being adapted for adjustment in rotation and side-to-side translation. A first lens displaying the patient's base prescription is mounted in one of the lens mounts. A second and third lens is mounted in the other two lens mounts. The second and third lenses each have a transition zone and a power ramp zone. The second and third lenses have surfaces that, when stacked together, create a standard progressive addition lens with a distance vision field, a reading vision field and transition region. When the second and third lenses are moved or rotated, the locations of the distance vision field, the reading vision field and the transition region are adjusted allowing the patient to experience a variety of distance vision fields and reading vision fields. In the second lens of the preferred embodiment, the form of the power ramp zone is a spiraling power, which is expressed in polar coordinates approximately by the thickness function:

$$T_{lens1}(r,\theta) \approx Cr^2(\theta-\theta_1)+T_0, \theta \in \text{power ramp}$$

and the form of the transition zone is:

$$T_{lens1}(r,\theta) \approx r^2 f(\theta)+T_0, \theta \in \text{transition zone}$$

where $T_0$ is a base thickness, $\theta_1$ is a base orientation, C is the ramp steepness, and the function $f(\theta)$ is picked to smoothly transition the two edges of the transition zone so that there is no discontinuity in the thickness, and also no discontinuity in slope. The form of the power ramp zone for the third lens is complimentary to the form of the power ramp zone for the first lens, and the form of the transition zone for the second lens has the same functional form.

BRIEF DESCRIPTION OF THE DRAWINGS

FIGS. 1a and 1B show features of a preferred embodiment of the present invention.

FIGS. 2A and 2B show power ramp zones and transition zones.

FIGS. 3A through 3E show how the lenses are adjusted to form progressive lenses.

FIGS. 4A and 4B show how the thickness of the lenses of the preferred embodiment vary with angle.

FIGS. 6A through 6H show how lenses are stacked to achieve particular results.

DETAILED DESCRIPTION OF PREFERRED EMBODIMENTS

Figure 5A:
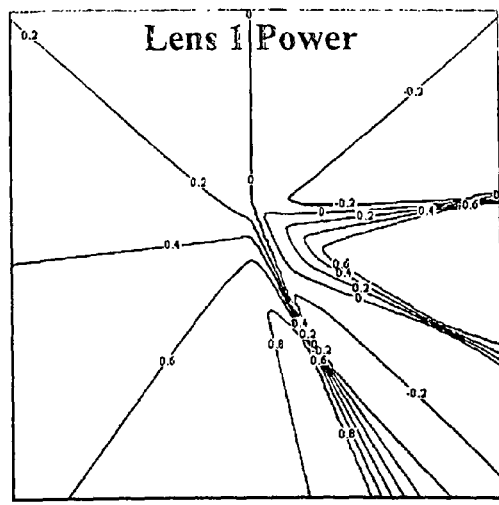
FIGS. 5A through 5D show a detailed design of two lenses for one eye.

Applicants have devised a device for determination of patient's progressive addition lens design preference (referred to hereinafter as "Test Unit") which can create an adjustable progressive addition effect which spans a design space adequate to determine the patient's progressive preference. This Test Unit uses two special and unique lenses in front of each eye in addition to a lens with the patient's base correction. The Test Unit consists of 6 lens mounts, with 3 per eye. Each lens mount shown at 4 in FIG. 1A contains a lens: one for the base prescription 1L and 1R and two for the adjustable progressive addition lens pair 2L and 3L and 2R and 3R as shown in FIG. 1B. Each mount is adjustable in rotation and horizontal side-to-side translation. The base prescription lenses 1L and 1R correct the power and astigmatism of the patient without any progressive correction. The adjustable progressive addition lenses 2L, 3L, 2R and 3R provide only the progressive add power but in a manner that is highly adjustable so that the patient's preferences regarding the progressive add power can be ascertained. There are 3 mounts on front of each eye, each independently adjustable. In this preferred embodiment the lenses are actuated with a conventional screw adjustment, with a gauge mechanism (not shown) to be read by the operator. The lenses are usually not mounted permanently, as there will be different base prescriptions and different progressive addition lens sets depending on the patient. The Test Unit includes earpieces 6 and a nose bridge 8. The nose bridge may have vertical actuation.

A challenge in creating this Test Unit which is not needed for most eye diagnostic equipment is a large field of view. The issue with the progressive addition lens is the performance as one looks in different directions; therefore the device must have a large unobstructed area yet which is lightweight and fits on the head.

The enabling breakthrough for this Test Unit is the adjustable progressive addition lens pair. In FIGS. 2A through 3E one of the adjustable progressive addition lens pair is shown as little square dots and the other of the pair is shown as dashes. Applicants have essentially devised a way to break apart the components of the left and right side of a progressive addition lens. When stacked together, the two lenses create a standard progressive addition lens. The various movements cause effects associated with progressive preference evaluation:

1. As shown in FIGS. 2A to 3E, when dashed lens is rotated, the left hand side transition region is rotated up or down.
2. When the dotted lens is rotated, the right hand side transition region is rotated up or down.
3. When the lenses are rotated together, the angle and location of the reading zone is moved.
4. When the lenses are rotated in opposite directions, the size of the distance and reading regions are traded off (3B and 3C).
5. When the lenses are moved laterally left or right together, the location of the corridor is moved.
6. When the lenses are moved laterally left or right but in opposite directions, the width vs. length of the corridor is varied (3D and 3E).

With each of these movements, various forms and magnitudes of distortions and aberrations are introduced and can be demonstrated to the patient.

Detailed Lens Designs

The lens designs of 2L and 3L and 2R and 3R use a unique azimuthal power spiral design. Each side of the design is performed in a similar way. Each of the lenses of 2L and 3L on the left side and 2R and 3R on the right side have a transition zone and a power ramp zone as shown in FIGS. 2A and 2B. The transition zone is essentially one of the sides of the progressive transition zone. The power ramp zone is the majority of the lens, and here the surface is dominated by a special spiraling function which produces lines of constant power along lines of constant angle from the center of the lens pair. The top part of the power ramp is designed for distance and the bottom of the power ramp is designed for reading. The corridor in the power ramp zone between the top and the bottom and between the two transition zones provide a smooth transition between the distance and reading zones.

The form of the power ramp zone is a spiraling power, which can be expressed in polar coordinates approximately by the thickness function:

$$T_{lens1}(r,\theta) \approx Cr^2(\theta-\theta_1)+T_0, \theta \in \text{power ramp}$$

The form of the transition zone is:

$$T_{lens1}(r,\theta) \approx r^2 f(\theta)+T_0, \theta \in \text{transition zone}$$

where the function is picked to smoothly transition the two edges of the transition zone so that there is no discontinuity in the thickness, and also no discontinuity in slope.

The complementary lens has the reverse of this power ramp, $$T_{lens2}(r,\theta) \approx Cr^2(\theta-\theta_2)+T_0, \theta \in \text{second power ramp}$$

When we combine the two lenses by stacking them, we need to keep track of the ambiguities of the angle with regard to $2\pi$ offsets. FIG. 4A plots the thicknesses of the two lenses at a constant distance from the center vs. azimuthal angle. When these functions are added in FIG. 4B, the ramps cancel, but there are two offset plateaus. These plateaus both have functional form given by $$T_{combined}(r,\theta) \approx Cr^2(\theta_2-\theta_1+2\pi N)+2T_0, \theta \notin \text{transition}$$

where N is an integer that depends on which plateau we are on and how we selected our coordinate system. The difference in thickness between the two plateaus is exactly one of the $2\pi$ offsets:

$$[T_{lens1}(r,\theta)+T_{lens2}(r,\theta)]_{plateau1} - [T_{lens1}(r,\theta)+T_{lens2}(r,\theta)]_{plateau2} = 2\pi Cr^2$$

This has the functional form of an add power.

Use of a single function created in this way produces a very abrupt transition between the distance and reading zones. The applicants have improved the above formalism by smoothing out the cusp region near r=0, thereby providing a more desired gradual transition.

Applicants have performed detailed designs using the following methodology:

1. Create a set of basic spiral ramps with transition functions as described above. The ramp functions are created by combining a ramp with functional form $r^2\theta$ with two transition zones with functional form $r^2(A\cos(2(\theta-\theta_0))+B)$ where the constants are picked to make the functions and first derivatives continuous.

2. The set of functions in 1) have different centers and different transition regions. The centers lie along the centerline of the corridor.
3. Add the set of functions together, effectively graduating the transition region, using a weighting function. The weighting function is determined by taste, and a constant weighting function will fulfill the purpose. We have found that a smooth weighting function which gives large weight to the functions with centers in the vertical center of the corridor, and likewise low weight to the functions with centers in the top and bottom of the corridor, to give the best results.

Figure 5B:
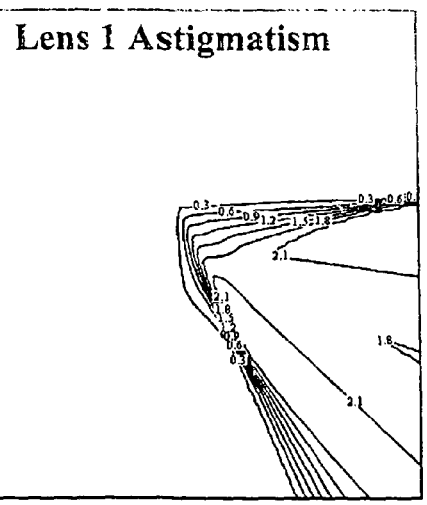
Figure 5C:
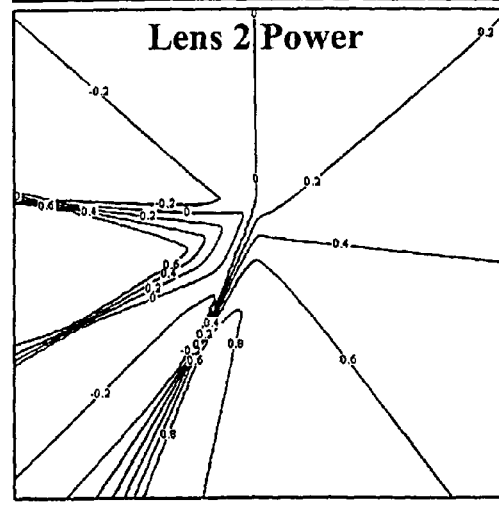
Figure 5D:
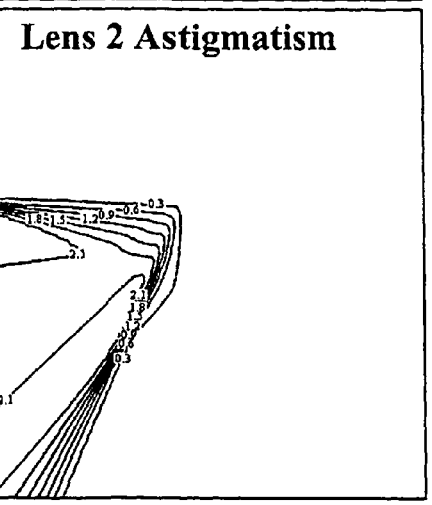

Applicants have computed these detailed designs and plotted the results for one eye. The results are shown in FIGS. 5A through 5D. 5A and 5C show sphere power and 5B and 5D show astigmatism which are the two most commonly plotted parameters when documenting progressive addition lens designs. In these plots the power varies from −0.32 Diopter to 0.85 Diopter and the astigmatism varies from 0.03 Diopter to 2.23 Diopter.

The detailed design of the FIG. 5 lenses use the following parameters:
1. The angle for which the transition region starts, measured from top vertical, varies from 62.6 degrees to 88.7 degrees for the set of spiral ramps. One of the lenses measures this angle clockwise, the other counterclockwise.
2. The ending angle of the transition region varies from 132.6 degrees to 158.7 degrees.
3. The transition regions for all of the spiral ramps are 70 degrees.
4. The corridor is taken to be vertical. The center position height for the set of spiral ramps varies from −4 to +4 mm.

Applicants next in FIGS. 6A through 6H show the result of stacking the lenses in slightly different orientations, which has the effect of adding the powers and astigmatisms assuming the lenses are placed closely together (typically less than 1 mm). The lenses are stacked in a few example configurations to demonstrate some of the parameter space. The following configurations are:
1. FIGS. 6A and 6B: Nominal configuration. In this configuration various parameters are somewhat balanced. The power varies from 0 to 1.5 Diopter, and the astigmatism varies from 0 to 2.25 Diopter.
2. FIGS. 6C and 6D: Wide Distance Zone configuration. The lenses are differentially rotated to make the distance zone larger and the reading zone smaller. The power varies from 0.08 to 1.58 Diopter, and the astigmatism varies from 0 to 2.28 Diopter.
3. FIGS. 6E and 6F: Wide Reading Zone configuration. The lenses are differentially rotated to make the reading zone larger and the distance zone smaller. The power varies from −0.17 to 1.42 Diopter, and the astigmatism varies from 0 to 2.26 Diopter.
4. FIGS. 6G and 6H: Wide Corridor configuration. The lenses are translated differentially side-to-side to make the corridor wider but longer. The power varies from 0 to 1.49 Diopter, and the astigmatism varies from 0 to 2.31 Diopter.

Different lens sets for different add powers would be required. The example shown above is for 1.5 Diopter add power, but different values can be scaled from the above design by a constant multiplier on the thickness. Most practitioners would find 1 to 3 diopters of add power in ½ diopter steps to be adequate.

Conversion of Measurement to Progressive Addition Lens Design

The patient's progressive addition lens preference parameters take the form of the following measurements:
1. Left Eye
   a. Rotation measured from the progressive rotation gauges:
      i. Relative angle: reading zone size vs. distance zone size
      ii. Common angles: preferred corridor angle
   b. Rotation measured from the base prescription rotation gauge:
      i. Astigmatism angle
   c. Translation measured from the progressive rotation gauges:
      i. Relative motion: corridor width vs. length
      ii. Common motion: corridor pupil distance from center
   d. Translation measured from the base prescription rotation gauge:
      i. Pupil distance
2. Right Eye:
   a. Same as left eye
   b. Same as left eye
   c. Same as left eye
   d. Same as left eye
3. Common Vertical Motion:
   a. Pupil height Of these, the measurements, 1.a., 1.c., 2.a., 2.c. ("progressive parameters") are used in the progressive part of the lens design. The other measurements may be redundant with previously obtained measurements of a patient's eye aberrations, eye related parameters, or patient eyeglass preference parameters ("base prescription"), but could also be used to achieve the base aspect of the design as well.

Once the patient's progressive addition lens preference is measured, the data must be converted into a lens design which will please the patient. Four ways of doing this are:
1. Adding the thicknesses plus the base prescription to nearly duplicate the Test Unit optical properties at the preferred settings.
2. Using the progressive parameters and base prescription as inputs to a design optimization routine.
3. Using the progressive parameters, base prescription, and the frame perimeter as inputs to a design optimization routine.
4. Using the progressive parameters to select from a set of existing progressive designs.

VARIATIONS

Although the present invention has been described above in terms of specific preferred embodiments, persons skilled in this art will recognize that many variations are possible within the general concepts of the present invention. For example up-down translation in many applications will not be necessary but could be included in a straightforward manner. In FIGS. 2A and 2B the two sides are typically similar but in some cases differences may be called for. Therefore, the scope of the present invention should be determined by the appended claims and not by the specific embodiments described above.

We claim:
1. A progressive addition lens demonstration device for demonstrating a variety of different progressive addition lenses to permit a patient to experience a variety of distance vision fields and reading vision fields, said device comprising:

A) a frame adapted to hold in place in front of each of a patient's eyes three lens mounts, defining a third lens mount, a first lens mount and a second lens mount, at least the second and third lens mounts being adapted for adjustment in rotation and side-to-side translation,
B) a third lens displaying the patients base prescription mounted in the third lens mount,
C) a first and second lens mounted respectively in the first and second lens mounts said first and second lenses, each having a transition zone and a power ramp zone and having complementary surfaces so that when stacked together they create a standard progressive addition lens with a distance vision field, a reading vision field and transition region, and when the first or second lenses are moved or rotated the locations of the distance vision field, the reading vision field and the transition region are adjusted allowing the patient to experience a variety of distance vision fields, reading vision fields, and transition regions;

wherein for the first lens, the form of the power ramp zone is a spiraling power, which is expressed in polar coordinates approximately by the thickness function:

$$T_{lens1}(r,\theta) \approx Cr^2(\theta-\theta_1)+T_0, \theta \in \text{power ramp}$$

and the form of the transition zone is:

$$T_{lens1}(r,\theta) \approx r^2 f(\theta)+T_0, \theta \in \text{transition zone}$$

where $T_0$ is a base thickness, $\theta$ is a base orientation, C is the ramp steepness and the function $f(\theta)$ is picked to smoothly transition the two edges of the transition zone so that there is no discontinuity in the thickness, and also no discontinuity in slope and where the form of the power ramp zone for the second lens is complementary to the form of the power ramp zone for the first lens, and the form of the transition zone for the second and third lenses have the same functional form.

2. A process for designing progressive addition lenses to permit a patient to experience a variety of distance vision fields and reading vision fields, comprising the steps of:
   A) using progressive addition lens design device comprising:
      1) a frame adapted to hold in place in front of each of a patient's eyes three lens mounts, each lens mounts being adapted for adjustment in rotation and side-to-side translation,
      2) a third lens displaying the patients base prescription mounted in one of the lens,
      3) a first and second lens mounted in the other two lens mounts said first and second lenses, each having a transition zone and a power ramp zone and having complementary surfaces so that when stacked together with the first lens they create a standard progressive addition lens with a distance vision field, a reading vision field and transition region, and when the first or second lenses are moved or rotated the locations of the distance vision field, the reading vision field and the transition region are adjusted;
   B) adjusting positions of the first and second lenses in order to allow the patient to experience a variety of distance vision fields and reading vision fields.

3. The process as in claim 2 and further comprising a step of adding the thicknesses of the lenses plus the base prescription to nearly duplicate the design device optical properties at the preferred settings.

* * * * *